United States Patent [19]

Appleton et al.

[11] 4,151,179
[45] Apr. 24, 1979

[54] 2-(4H-1-BENZOPYRAN-6-YL)PROPIONIC ACIDS

[75] Inventors: Richard A. Appleton; Kevan Brown, both of Loughborough, England

[73] Assignee: Fisons Limited, London, England

[21] Appl. No.: 712,603

[22] Filed: Aug. 9, 1976

Related U.S. Application Data

[63] Continuation-in-part of Ser. No. 557,897, Mar. 12, 1975, Pat. No. 4,057,641.

[30] Foreign Application Priority Data

Aug. 22, 1975 [GB] United Kingdom ............... 34871/70
Aug. 22, 1975 [GB] United Kingdom ............... 34872/70

[51] Int. Cl.² .................... C07D 311/22; A61K 31/35
[52] U.S. Cl. ................................. 260/345.2; 424/283
[58] Field of Search ...................... 260/345.2

[56] References Cited

U.S. PATENT DOCUMENTS 4,065,467  12/1977  Doria et al. ...................... 260/345.2

FOREIGN PATENT DOCUMENTS 826765  9/1975  Belgium ............................... 260/345.2

OTHER PUBLICATIONS

Briet et al., Chem. Abstract, 85, 123, 766s (1976) (Abstract of Ger. Offen. 2,549,745).
Matshoka et al., Nippon Kagaku Zasshi, 78, 651 (1957).
Patel et al., J. Indian Chem. Soc., 50, 295 (1973).
Dare, Ann. Chim. (Rome), 48, 762 (1958).

*Primary Examiner*—Nicky Chan
*Attorney, Agent, or Firm*—Merriam, Marshall & Bicknell

[57] ABSTRACT

There are described compounds of formula I,

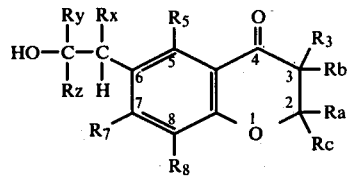

in which Ra is hydrogen, alkyl, alkenyl or phenyl,
$R_3$, $R_5$, $R_7$ and $R_8$, which may be the same or different, are each hydrogen, alkyl, alkoxy, halogen, hydroxy, alkenyl or phenyl,
Rx is hydrogen or alkyl,
Ry and Rz are both hydrogen, or together represent a carbonyl oxygen atom,
Rb and Rc are both hydrogen or together represent a carbon-carbon bond,
provided that when Rx is hydrogen, Ry and Rz together represent a carbonyl oxygen atom and $R_5$, $R_7$ and $R_8$ are all hydrogen then Ra is other than methyl or phenyl,
and pharmaceutically acceptable derivatives thereof.

There are also described methods for making the compounds and pharmaceutical, e.g. anti-inflammatory, compositions containing the compounds.

15 Claims, No Drawings

2-(4H-1-BENZOPYRAN-6-YL)PROPIONIC ACIDS

This application is a continuation-in-part of application Ser. No. 557,897 filed Mar. 12, 1975, now U.S. Pat. No. 4,057,641.

This invention relates to new compounds, methods for their preparation and compositions containing them.

According to our invention we provide compounds of formula I,

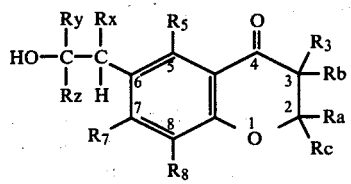

in which Ra is hydrogen, alkyl, alkenyl or phenyl, $R_3$, $R_5$, $R_7$ and $R_8$, which may be the same or different, are each hydrogen, alkyl, alkoxy, halogen, hydroxy, alkenyl or phenyl, Rx is hydrogen or alkyl, Ry and Rz are both hydrogen, or together represent a carbonyl oxygen atom, Rb and Rc are both hydrogen or together represent a carbon-carbon bond, provided that when Rx is hydrogen, Ry and Rz together represent a carbonyl oxygen atom and $R_5$, $R_7$ and $R_8$ are all hydrogen then Ra is other than methyl or phenyl, and pharmaceutically acceptable derivatives thereof.

According to our invention we also provide a process for the production of a compound of formula I, or a pharmaceutically acceptable derivative thereof, which comprises (a) producing a compound of formula Ia,

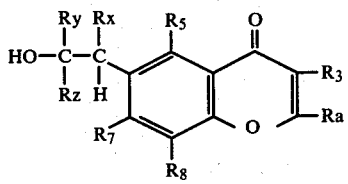

in which Ra, Rx, Ry, Rz, $R_3$, $R_5$, $R_7$ and $R_8$ are as defined above, by cyclising a compound of formula II,

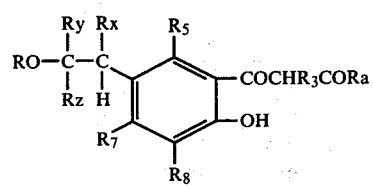

in which Ra, Rx, Ry, Rz, $R_3$, $R_5$, $R_7$ and $R_8$ are as defined above, and R is hydrogen or an alcoholic residue when Ry and Rz together represent carbonyl oxygen, and R is hydrogen when Ry and Rz are both hydrogen, (b) producing a compound of formula Ib,

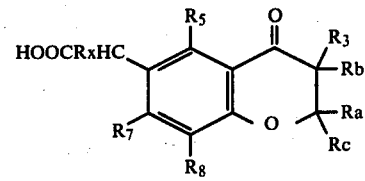

in which Ra, Rb, Rc, Rx, $R_3$, $R_5$, $R_7$ and $R_8$ are as defined above, by (i) selectively oxidising a corresponding compound of formula Ic,

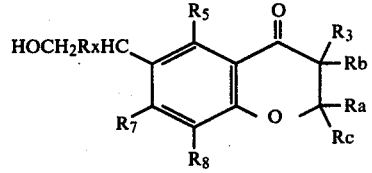

in which Ra, Rx, Rb, Rc, $R_3$, $R_5$, $R_7$ and $R_8$ are as defined above, or (ii) hydrolysing a corresponding ester of a compound of formula Ib, (c) producing a compound of formula Id,

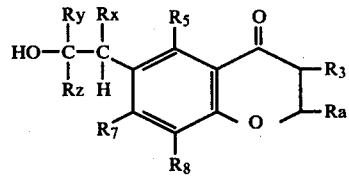

or an ester thereof, in which $R_3$, $R_5$, $R_7$, $R_8$, Ra, Rx, Ry and Rz are as defined above, by selective reduction of a corresponding compound of formula Ia, or an ester thereof, (d) cyclising a compound of formula VII,

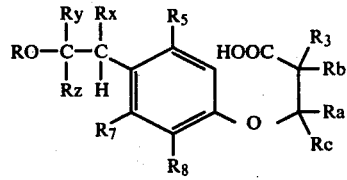

in which R, $R_3$, $R_5$, $R_7$, $R_8$, Ra, Rb, Rc, Rx, Ry and Rz are as defined above, or (e) producing a compound of formula Id by cyclising a compound of formula VIII,

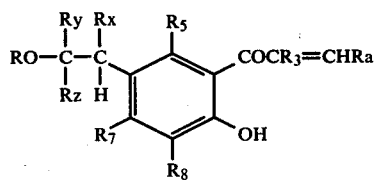

in which $R_3$, $R_5$, $R_7$, $R_8$, Ra, Rx, Ry, Rz and R are as defined above, and where desired or necessary converting the compound of formula I to a pharmaceutically acceptable derivative thereof, or vice versa.

Process (a) may be carried out by heating, or under basic or neutral conditions. It is however preferred to carry out the cyclisation is the presence of an acid, e.g. hydrochloric acid, an in a solvent which is inert under the reaction conditions, e.g. a lower alkanol such as ethanol, or a water miscible ether such as dioxan or tetrahydrofuran. The reaction may be carried out at from about 20° to 150° C. When a compound of formula II in which R is an alcoholic residue is used as starting material, the alcoholic residue is usually removed during the cyclisation, however the product in which the alcoholic residue is still present may, if desired, be separated and used as such or may be further hydrolysed to the free acid. Suitable alcoholic residues include those containing up to an including 10 carbon atoms, e.g. a lower alkyl group or a benzyl group.

Process (b)(i) may be carried out using a suitable selective oxidising agent known to oxidise a —$CH_2OH$ group to a —COOH group. Thus for example a suitable oxidising agent comprises an aqueous mixture of chromium trioxide and sulphuric or acetic acid. The reaction may be carried out in a water miscible organic solvent, e.g. acetone, at a temperature of from about 10° to 30° C. The oxidation passes through the corresponding aldehyde which is usually present in the reaction mixture in the form of a metal complex and which is usually not isolated.

Process (b)(ii) may be carried out using conventional techniques, for example under mildly basic conditions, e.g. using sodium carbonate, sodium bicarbonate or sodium hydroxide, or under acidic conditions, e.g. a mixture of aqueous dioxan and hydrochloric acid. The ester may be any suitable ester of the —$CHR_x$ COOH group, e.g. an ester derived from an alcohol containing up to and including 10 carbon atoms, e.g. a lower alkyl or a benzyl ester.

Process (c) may be carried out using conventional techniques, e.g. by catalytic hydrogenation using a Raney nickel or a palladium (e.g. 5% Pd on $BaSO_4$) catalyst at a temperature of from about 20° to 50° C. at a pressure of from about 20 to 100 psi.

The cyclisation of process (d) may be carried out by treating the appropriate compound of formula VII with a cyclising agent, for example a dehydrating agent such as chlorosulphonic, polyphosphoric or sulphuric acid. The reaction is preferably carried out under anhydrous conditions and may be carried out at a temperature of from about 0° to 100° C. Alternatively cyclisation may be achieved by converting the free carboxy group of the compound of formula VII to an acyl halide group and subjecting the resulting acyl halide to an intramolecular cyclisation reaction.

The cyclisation of process (e) may be carried out under acidic, or preferably basic conditions, e.g. in the presence of an aqueous alkali metal hydroxide such as sodium hydroxide. The reaction may also be carried out in the presence of a water miscible solvent, e.g. a lower alkanol such as ethanol. The reaction is preferably carried out at a temperature of from about 10° to 60° C.

Compounds of formula II may be made by reacting a compound of formula IV,

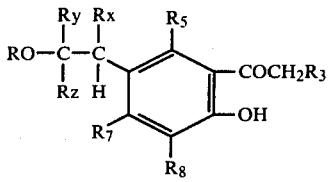

in which R, $R_x$, $R_y$, $R_z$, $R_3$, $R_5$, $R_7$ and $R_8$ are as defined above,
with a compound of formula V,

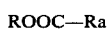

ROOC—Ra    V in which R and Ra are as defined above, under conditions conventionally used in similar reactions.

Compounds of formula IV may be made from known compounds using conventional techniques known per se, for example using Friedel-Crafts reaction conditions and reacting an appropriately substituted acyl chloride with a compound of formula VI,

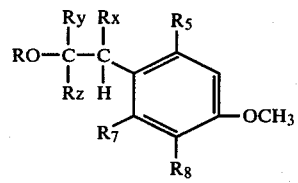

in which R, $R_x$, $R_y$, $R_z$, $R_5$, $R_7$, and $R_8$ are as defined above, and where necessary hydrolysing the resulting product.

Compounds of formula VII may be made by reacting a compound of formula X,

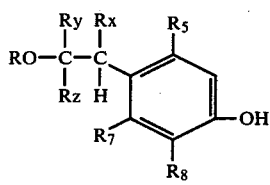

in which R, $R_x$, $R_y$, $R_z$, $R_5$, $R_7$ and $R_8$ are as defined above,
with a compound of formula (ROOC)$RbR_3$C—CX-RaRc or of formula (ROOC)RbC=CRaRc, in which formulae R, Ra, Rb, Rc and $R_3$ are as defined above and X is a halogen atom. This reaction may be carried out under basic conditions and may, if necessary, be followed by hydrolysis of the ester group. Compounds of formula VII in which Rb and Rc are both hydrogen may be made by reduction of a corresponding compound of formula VII in which Rb and Rc together form a carbon-carbon bond, e.g. using sodium amalgam.

Compounds of formula VIII may be made by reacting a compound of formula VI with a compound RaCH=$CR_3$COCl in which Ra and $R_3$ are as defined above. The reaction may be carried out in the presence of a Friedel-Crafts catalyst, e.g. titanium tetrachloride, in a chlorinated hydrocarbon solvent, e.g. tetrachlorethane or dichloromethane, at a temperature of about $-15°$ C. The ether —$OCH_3$ group may then be cleaved. e.g. by the addition of boron trichloride.

Compounds of formulae V, VI and X are either known or may be made from known compounds using techniques known per se.

The compounds of formula I and intermediates therefore may be isolated and purified using techniques known per se, e.g. crystalisation. Those of the compounds of formula I which are acidic may be purified by conversion to a suitable, e.g. an amine, salt; recrystalisation of the salt and regeneration of the free acid by treatment of the salt with a suitable acid.

Pharmaceutically acceptable derivatives of the compounds of formula I include pharmaceutically acceptable salts, esters and amides of those compounds in which Ry and Rz together form a carbonyl oxygen atom. Suitable salts include ammonium, alkali metal (e.g. sodium, potassium and lithium) and alkaline earth metal salts (e.g. calcium or magnesium), and salts with suitable organic bases, e.g. salts with lower alkylamines such as methylamine or ethylamine, with substituted lower alkylamines, e.g. hydroxy substituted alkylamines or with simple monocyclic nitrogen heterocyclic compounds, e.g. piperidine or morpholine. Suitable esters include simple esters derived from alcohols containing up to and including 10 carbon atoms, e.g. lower alkyl esters. The esters may be made by conventional techniques, e.g. esterification, transesterification or reaction of the acid, or a salt thereof, with an appropriate compound containing a good leaving group. The salts may be made by basification of the free acid, basic hydrolysis of an ester or by a metathetical process. The amides may be made by reaction of a corresponding ester, e.g. a lower alkyl ester, with ammonia or with an appropriate amine, e.g. a mono - or di-alkyl C1 to 6 amine.

The compounds of formula I, and pharmaceutically acceptable derivatives thereof, are useful because they possess pharmacological activity in animals. In particular the compounds are useful as anti-inflammatory agents as indicated by the carrageenan-induced edema test in rats (C A Winter et al, Proc. Soc. Exp. Biol. Vol.111, page 544, 1962). The compounds are therefore useful in the treatment of painful inflammation of the joints and periarticular tissue such as occurs in rheumatoid arthritis, Stil's disease, osteoarthritis, various types of non-specific inflammatory or rheumatic conditions affecting the fibro muscular tissue and connective tissue and rheumatic fever and its sequelae. In those cases in which the above conditions include pain, pyrexia, and puritis, coupled with inflammation, the present compounds are useful for the relief of these associative conditions as well as the principal condition.

For the above mentioned uses the dosage administered will, of course, vary with the compound employed, the mode of administration and the treatment desired. However, in general satisfactory results are obtained when the compounds are administered at a daily dosage of from about 0.1 mg to about 30 mg and preferably from 0.1 mg to 20 mg per kg of animal body weight, preferably given in divided doses 1 to 4 times a day or in sustained release form. For man the total daily dose is in the range of from about 7.0 mg to about 2,100 mg and preferably from 7.0 mg to 1,400 mg and unit dosage forms suitable for oral administration comprise from about 2.0 mg to about 1,400 mg of the compound admixed with a solid or liquid pharmaceutical carrier or diluent.

The compounds of formula I, and pharmaceutically acceptable derivatives thereof, may be used on their own or in the form of appropriate medicinal preparations for enteral, parenteral or topical administration. Thus the new compounds may be worked up with inorganic or organic, pharmaceutically acceptable adjuvants, diluents or carriers. Examples of such adjuvants, diluents and carriers are:- for tablets and dragees: lactose, starch, talc, stearic acid; for capsules: tartaric acid or lactose; for injectable solutions: water, alcohols, glycerin, vegetable oils; for suppositories: natural or hardened oils or waxes. We prefer the composition to be in a form suitable for oral administration. We also prefer the composition to contain up to 50% and more preferably up to 25% by weight of the compound of formula I, or of the pharmaceutically acceptable derivative thereof.

It is well known that many anti-inflammatory agents currently in use have unwanted gastro-intestinal side effects. The compounds of the present invention have, in general, been found in animal tests to have a lower incidence of side effects than some other anti-inflammatory agents.

Some of the compounds of formula I have one or more asymmetric carbon atoms and may therefore exist in the form of two or more (depending on the number of asymmetric carbon atoms) optical isomers, or a racemic or other mixtures of such isomers. The various optical isomers may be resolved, wholly or partially, using conventional techniques, e.g. formation of a salt of an acidic compound of formula I with a optically active base, e.g. cinchonidine, fractional crystallisation of the salt and subsequent regeneration of the free acid.

We prefer each of Ra, Rx, $R_3$, $R_5$, $R_7$ and $R_8$ to contain up to 10, and preferably up to 6 carbon atoms. In particular we prefer Ra to comprise a chain of at least 2 carbon atoms, such a chain optionally being substituted by alkyl on the atom adjacent to the chromone or chromanone nucleus. Thus Ra preferably contains from 2 to 10, and more preferably from 2 to 6 carbon atoms. In particular Ra may be straight or branched alkyl C 1 to 4 and especially straight or branched alkyl C 2 to 3. Specific examples of Ra which may be mentioned are n-propyl and phenyl, and preferably methyl, ethyl, isopropyl and hydrogen. Preferred values for $R_3$ are phenyl and alkyl, and more preferably hydrogen or methyl. We also prefer each of $R_5$, $R_7$ and $R_8$ to be selected from hydrogen, hydroxy, alkoxy and halogen, e.g. to be hydrogen, hydroxy, methoxy, ethyl or chlorine. We particularly prefer each of $R_5$, $R_7$ and $R_8$ to be hydrogen or one or $R_5$, $R_7$ and $R_8$ to be chlorine or methoxy and the remainder to be hydrogen. We prefer Rx to contain up to and including 2 carbon atoms, e.g. to be ethyl or preferably methyl. We also prefer Ry and Rz to together form a carbonyl oxygen atom (i.e. we prefer substituted and unsubstituted acetic acid derivatives, e.g. propionic acid derivatives), and Rb and Rc both to represent hydrogen (i.e. chromanone compounds).

As a specific group of compounds of formula I we provide compounds of formula Ie,

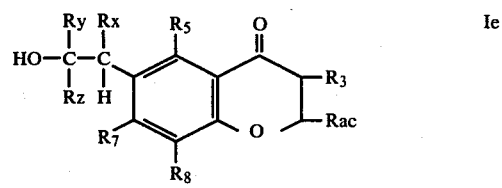

in which $R_3$, $R_5$, $R_7$, $R_8$, Rx, Ry and Rz are as defined above, and

Rac is hydrogen, alkyl C 2 to 6 or alkenyl, and pharmaceutically acceptable derivatives thereof.

The invention is illustrated but in no way limited by the following Examples.

EXAMPLE 1

2-(2-Ethyl-4-oxo-4H-1-benzopyran-6-yl)ethan-1-ol (a) 2-(3-Acetyl-4-hydroxyphenyl)ethyl acetate Aluminium chloride (90 g) was added portionwise to a stirred solution of 4-methoxyphenethyl alcohol (29.2 g) and acetyl chloride (40 mls) in 1,1,2,2-tetrachloroethane (300 mls), cooled in an ice-bath, at a rate sufficient to maintain the temperature between 0° and +5° C. The mixture was stirred at room temperature for 22 hours before pouring on to crushed ice and separating the two phases. The aqueous phase was extracted with ether (3x) and the combined organic extracts were washed with water, saturated brine solution, and dried over anhydrous magnesium sulphate. Evaporation of the solvent yielded the crude product as a pale yellow oil. Vacuum distillation furnished a colourless oil bp 120°–121°/0.15 mm (35.7 g; 83%).

The i.r. spectrum showed carbonyl bands at 1648 and 1742 $cm^{-1}$.

(b) 3-Acetyl-4-hydroxyphenethyl alcohol

A solution of 2-(3-acetyl-4-hydroxyphenyl)ethyl acetate (35.7 g) in ethanol (400 ml), and sodium bicarbonate (42 g) in water (200 mls) was refluxed for 8½ hours. The ethanol was removed on a 'Rotavapor' and the residue was extracted with ether (3x). The combined ethereal extracts were washed with water, sodium bicarbonate solution, saturated brine solution, dried over anhydrous magnesium sulphate, and evaporated to yield a red oil (31.3 g). The oil was recrystallised from hexane and ether (4:1) to yield the product as a pale yellow crystalline solid (18.3 g). The mother liquors were concentrated and an additional batch of product was obtained as a pale yellow crystalline solid (9.3 g).

The i.r. spectrum showed a carbonyl band at 1645 $cm^{-1}$.

(c) 2-(2-Ethyl-4-oxo-4H-1-benzopyran-6-yl)ethan-1-ol

Sodium hydride (14.4 g; 50% dispersion in oil) was washed free from oil by decantation with dry ether (3x) and hexamethylphosphoramide (30 ml) was added. 2-(3-Acetyl-4-hydroxyphenyl)ethanol (9 g) in dry hexamethylphosphoramide (85 mls) was added to the resulting stirred slurry at a rate sufficient to maintain the temperature between +20° and +25° C. When evolution of hydrogen had ceased, ethyl propionate (10.2 g) was added and the green solution was stirred at room temperature for 4 hours. Water was then added followed by dilute hydrochloric acid. The product was extracted with ether and washed with a small amount of water. The combined aqueous solutions were saturated with sodium chloride and reextracted with ether. The combined ethereal solutions were dried over anhydrous magnesium sulphate and evaporation of the solution yielded 2-[4-hydroxy-3-(3-oxapentanoyl)phenyl]ethanol as a red oil. The red oil was refluxed in ethanol (50 mls) and concentrated hydrochloric acid (20 mls) for 1 hour. The ethanol was removed on a 'Rotavapor' and the residue was extracted with chloroform (3x). The chloroform solution was dried over anhydrous magnesium sulphate and evaporated to yield a red oil. The oil was dissolved in hot benzene, charcoaled and recrystallised from benzene and n-hexane (1:4) to yield the product as an off-white solid (4.1 g) mp 75°–76° C.

Found: C, 71.5% H, 6.5%; $C_{13}H_{14}O_3$ requires: C, 71.5% H, 6.7%.

IR, NMR and MS were consistent with the proposed structure. The i.r. carbonyl absorption was at 1660 $cm^{-1}$.

EXAMPLE 2

(2-Ethyl-4-oxo-4H-1-benzopyran-6-yl)acetic acid

Jones Reagent was prepared by adding concentrated sulphuric acid (11.5 mls) carefully to a solution of chromium trioxide (13.4 g) in water (20 ml). When cool, the mixture was diluted to a volume of 50 mls with water to yield a clear deep red solution.

This red solution was added dropwise to a stirred solution of 2-(2-ethyl-4-oxo-4H-1-benzopyran-6-yl)ethan-1-ol (3.5 g) in acetone (30 mls) maintained at 20° C. until a permanent red colouration was obtained. The reaction was stirred at room temperature for a further 1½ hours. Water was added and the product was extracted with ether (3x). The separated ethereal solution was extracted with sodium bicarbonate which was washed with water, acidified with dilute hydrochloric acid and extracted with chloroform. The chloroform solution was washed with a small volume of saturated brine solution and dried over anhydrous magnesium sulphate. Evaporation of the solvent yielded the product as an off-white solid (2.2 g). Recrystallisation from benzene yielded pale yellow needle crystals mp 171°–172° C. (1.1 g). The mother liquors were concentrated and a second crop was obtained as a pale yellow solid (0.6 g).

Found: C, 67.0%; H, 5.3%; $C_{13}H_{13}O_4$ requires: C, 67.3; H, 5.2%.

Nmr, ir and ms consistent with the proposed structure.

EXAMPLE 3

2-(2-Ethyl-4-oxo-4H-1-benzopyran-6-yl)propan-1-ol (a) Methyl 2-(4-methoxyphenyl)propionate Sodium hydride (6.2 g; 0.258 mol) was suspended in dry hexamethylphosphoramide (45 ml) and 4-hydroxyphenylacetic acid (12.4 g; 0.0815 mol), dissolved in hexamethylphosphoramide (100 ml), was slowly added to the stirred slurry so that the temperature was at 15°±5° C. The solution was stirred for 75 mins then methyl iodide (35 ml; 79.5 g; 0.56 mol) was added at a rate sufficient to maintain the temperature below 28°. Stirring at ambient temperature was then continued for 15 hours. Water (400 ml) and 10% hydrochloric acid (400 ml) were added and the mixture was extracted with ether (2×300 ml). The combined ether extracts were washed with saturated sodium bicarbonate solution, with water until neutral, and then dried over magnesium sulphate. Evaporation of the solvent gave a pale yellow oil. (15.8 g). The nmr spectrum showed methyl absorption at τ6.33 and 6.49 (singlets) and at τ8.62 (doublet, J=6 cps). The ir spectrum showed a carbonyl absorption at 1740 $cm^{-1}$.

(b) 2-(4-Methoxyphenyl)propan-1-ol

Methyl 2-(4-methoxyphenyl)propionate (11.39 g; 0.0586 mol) was dissolved in dry ether (25 ml) and slowly added to a stirred suspension of lithium aluminium hydride (4.59 g; 0.121 mol;) in dry ether (60 ml); the temperature was maintained below 25° C. by cooling. Stirring at ambient temperature was continued for 1 hour. Water was cautiously added dropwise to decompose the unreacted lithium aluminium hydride and the inorganic salts were dissolved by the addition of dilute hydrochloric acid. The ether was separated and the aqueous phase re-extracted with ether (2×100 ml). The combined ether extracts were washed with water, saturated sodium bicarbonate solution, water, and then dried over magnesium sulphate. The product was isolated as a pale yellow oil (8.72 g) following evaporation of the solvent.

The n.m.r. spectrum showed methyl absorption at $\tau 6.35$ (singlet) and at $\tau 8.85$ (doublet J = 6 cps); it showed the CH$_2$OH absorption at $\tau 6.60$ (doublet J = 8 cps).

(c) 2-(3-Acetyl-4-hydroxyphenyl)propyl acetate 2-(4-Methoxyphenyl)propan-1-ol (17.45 g; 0.106 mol) and acetyl chloride (23 ml; 25.3 g; 0.323 mol) were dissolved in 1,1,2,2-tetrachloroethane (250 ml). Aluminum chloride (60.0 g; 0.451 mol) was added batchwise with stirring at a rate sufficient to maintain the temperature below 35° C. Stirring was continued at ambient temperature for 18 hours. The reaction mixture was poured into iced saline solution and extracted with ether (2×600 ml). The combined ether extracts were washed with saturated sodium bicarbonate solution, brine, and then dried over magnesium sulphate. The solvent was removed in vacuo leaving the product (20.05 g; 80% yield) as a pale brown oil.

The ir spectrum showed carbonyl absorptions at 1640 and 1740 cm$^{-1}$.

(d) 2-(3-Acetyl-4-hydroxyphenyl)propan-1-ol 2-(3-Acetyl-4-hydroxyphenyl)propyl acetate (20.0 g; 0.0847 mol) and sodium bicarbonate (25.4 g; 0.31 mol) were dissolved in ethanol (200 ml) and water (150 ml), and the mixture was refluxed for 20 hours. Ethanol was removed in vacuo and the residue was extracted with ether (3×150 ml). The combined ether extracts were washed with water, saturated sodium bicarbonate solution, brine, and then dried over magnesium sulphate. The product, after removing solvent, was chromatographed on silica gel using ether as eluent to give a pale brown oil (15.0 g; 72% yield).

The i.r. spectrum showed a carbonyl band at 1642 cm$^{-1}$.

(e) 2-(2-Ethyl-4-oxo-4H-1-benzopyran-6-yl)propan-1-ol 2-(3-Acetyl-4-hydroxyphenyl)propan-1-ol (15.0 g; 0.077 mol) was dissolved in hexamethylphosphoramide (150 ml) and slowly added to a stirred slurry of sodium hydride (10.0 g; 0.417 mol) in hexamethylphosphoramide (40 ml) at a rate sufficient to maintain the temperature below 25° C. Ethyl propionate (20.0 g; 0.2 mol) was added and the mixture stirred for 2 hours before pouring into 2N hydrochloric acid (600 ml). The solution was extracted with ether (2×300 ml) and the extracts evaporated to give 2-[4-hydroxy-3-(3-oxopentanoyl)-phenyl]propan-1-ol as a yellow oil. This was dissolved in ethanol (100 ml) containing concentrated hydrochloric acid (20 ml) and the solution was refluxed for 30 mins. The ethanol was removed in vacuo and the aqueous phase extracted with chloroform (2×150 ml). The combined extracts were washed with saturated sodium bicarbonate solution and dried over magnesium sulphate. The solvent was removed and the resulting oil was chromatographed on a silica gel column using ether as eluent. Recrystallisation of the product using hexane/ether (2:1) furnished a white microcrystalline solid (5.0 g) mp 59.5°-60.5° C.

C$_{14}$H$_{16}$O$_3$ requires: C. 72.5%, H. 6.9%. Found: C. 72.8%, H. 7.1%.

EXAMPLE 4

2-(2-Ethyl-4-oxo-4H-1-benzopyran-6-yl)propionic acid 2-(2-Ethyl-4-oxo-4H-1-benzopyran-6-yl)propan-1-ol (3.0 g; 0.0129 mol) was dissolved in acetone (20 ml) and Jones Reagent (Example 2) was slowly added until the solution attained a permanent brown colour. Water (100 ml) was added and the mixture was extracted with chloroform (4×70 ml). The combined chloroform phases were extracted with saturated sodium bicarbonate solution (4×30 ml). The aqueous phases were combined, washed with chloroform (100 ml) and then acidified with concentrated hydrochloric acid. The precipitated product was extracted with chloroform (3×100 ml) and the combined extracts dried over magnesium sulphate. After removing solvent, the product was recrystallised from benzene/hexane (1;1) to yield a pale yellow amorphous solid (1.4 g) mp 128°-128.5°.

C$_{14}$H$_{14}$O$_4$ requires: C. 68.3% H. 5.7%. Found: C. 68.1% H. 5.9%.

EXAMPLE 5

2-(2,3-Dihydro-2-ethyl-4-oxo-4H-1-benzopyran-6-yl)propanol 2-(2-Ethyl-4-oxo-4H-1-benzopyran-6-yl)propan-1-ol (4.1 g) was taken up in ethanol (100 ml), Raney Nickel (5.0 g) was added and the mixture hydrogenated at 45 psi for 2 hours. The catalyst was removed by filtration (Hyflo supercel) and replaced with a fresh batch (5.0 g) and hydrogenation at 45 psi continued for a further 3 hours. The catalyst was removed by filtration and the filtrate evaporated to yield 2-(2,3-dihydro-2-ethyl-4-oxo-4H-1-benzopyran-6-yl)propanol as a pale green oil (4.5 g), I.R. carbonyl absorption 1690 cms$^{-1}$.

The crude product was treated with Jones reagent, as described in Example 2, affording a pale yellow oil (2.7 g) which was purified by chromatography on silica gel using ether as eluant. Trituration with petroleum ether (bp 40°-60° C.) afforded a white solid (1.64 g) mp 75.5°-8° C.

C$_{14}$H$_{16}$O$_4$ requires: C, 67.7% H, 6.5%. Found: C, 67.7% H, 6.7%.

EXAMPLE 6

2-(2,3-Dihydro-2-ethyl-4-oxo-4H-1-benzopyran-6-yl)propionic acid

Methyl-2-(4-methoxyphenyl)propionate (22.0 g) was dissolved in dichloromethane (330 ml) and titanium tetrachloride (100.12 g, 58 ml) was added dropwise with stirring and cooling. The temperature being maintained at −15° C. to −10° C. After stirring the red-brown mixture for 10 minutes pent-2-enoylchloride (20.15 g) was added dropwise, again keeping the temperature between −15° C. and −10° C. The reaction mixture was stirred until the starting material had been consumed (as shown by thin layer chromatography silica gel: chloroform).

Boron trichloride (20 ml) was added at −15° C. and the reaction mixture allowed to warm up to 5° C. and poured onto a mixture of ice and concentrated hydrochloric acid and stirred vigorously for 30 minutes to ensure complete destruction of the organo metallic complexes. The dichloromethane was separated and the aqueous phase extracted with dichloromethane. The combined dichloromethane extracts were washed with sodium bicarbonate solution, dried and evaporated affording the intermediate methyl 2-[4-hydroxy-3-(pent-2-enoyl)phenyl]propionate as an oil.

The oil was taken up in ethanol (500 ml) and stirred with 10% aqueous sodium hydroxide solution (136 ml) at room temperature for 2 hours. The solution was acidified and the ethanol removed in vacuo. The aqueous residue was extracted with ether and the combined ethereal extracts were dried. The drying agent was removed by filtration. The ethereal filtrate was treated with dicyclohexylamine (21 g) and the solid salt removed by filtration. The free acid was regenerated by stirring in an ether/2N hydrochloric acid (1:1) mixture for 3 hours at room temperature. The dicyclohexylamine hydrochloride was removed by filtration and the filtrate worked up for acidic material, using ether as the solvent, affording the crude product (16.9 g) as a brown oil. This oil was recrystallised from ether/hexane to yield the desired product (10.3 g) mp 74°–5° C.

EXAMPLE 7

2-(2,3-Dihydro-2-isopropyl-4-oxo-4H-1-benzopyran-6-yl) propionic acid (a) Methyl 2-(3-acetyl-4-hydroxyphenyl)propionate Titanium tetrachloride (82.3 mls) was added dropwise to a stirred solution of methyl 2-(4-methoxyphenyl)propionate (25 g) in dry dichloromethane (250 mls), cooled in an ice/salt-bath, at a rate sufficient to maintain the temperature between $-10°$ C. and $-5°$ C. The mixture was stirred for 10 minutes and acetyl chloride (10 g) was added dropwise at a rate sufficient to maintain the temperature below 0° C. The solution was stirred at $-5°$ C. for 1½ hours when boron trichloride (15 mls) was added. Stirring was continued for ½ hour at $+3°$ C. before pouring on to crushed ice/concentrated hydrochloric and separating the two phases. The aqueous phase was extracted with ether (3x) and the combined organic extracts were washed with saturated sodium bicarbonate solution, saturated brine solution, and dried over anhydrous magnesium sulphate. Evaporation of the solvent yielded the crude product as a pale yellow oil. Vacuum distillation furnished a pale yellow oil bp 120°–125° C./0.15 mm (16.2 g; 59%)

The i.r. spectrum showed carbonyl bands at 1643 and 1735 cm$^{-1}$ (b) Methyl 2-(2-isopropyl-4-oxo-4H-1-benzopyran-6-yl)propionate Sodium hydride (18.5 g; 50% dispersion in oil) was washed free from oil by decantation with dry ether (3x): Methyl 2-(3-acetyl-4-hydroxyphenyl)propionate (16.2 g) in dry hexamethylphosphoramide (40 mls) was added to the resulting stirred slurry at a rate sufficient to maintain the temperature between $+20°$ C. and $+25°$ C. When evolution of hydrogen had ceased, ethyl isobutyrate (27 mls) was added dropwise at a rate sufficient to maintain the temperature between $+20°$ C. and $+25°$ C., and the solution was stirred at room temperature overnight. Water was then added, followed by dilute hydrochloric acid and ethanol (100 mls). The solution was refluxed for 45 minutes, the ethanol was evaporated on a 'Rotavapor' and the aqueous residue was extracted with ether (3x). The combined organic extracts were washed with sodium bicarbonate solution, saturated brine solution and dried over anhydrous magnesium sulphate. Evaporation of the solvent yielded methyl 2-(2-isopropyl-4-oxo-4H-1-benzopyran-6-yl)propionate as a red oil (5.4 g; 25%). The i.r. spectrum showed carbonyl bands at 1650 cm$^{-1}$ and 1730 cm$^{-1}$.

(c) Methyl 2-(2,3-dihydro-2-isopropyl-4-oxo-4H-1-benzopyran-6-yl) propionate

Raney Nickel (10.0 g) was added to methyl 2-(2-isopropyl-4-oxo-4H-1-benzopyran-6-yl)propionate (10.7 g) in dry ethanol (100 mls) and hydrogenated at 45 p.s.i. until uptake of hydrogen ceased. The Raney Nickel was filtered off and the solvent evaporated to yield the crude methyl 2-(2,3-dihydro-2-isopropyl-4-oxo-4H-1-benzopyran-6-yl) propionate as a pale green oil (9.2 g; 90%).

The i.r. spectrum showed carbonyl bands at 1690 cm$^{-1}$ and 1730 cm$^{-1}$.

(d) 2-(2,3-Dihydro-2-isopropyl-4-oxo-4H-1-benzopyran-6-yl) propionic acid

Sodium bicarbonate (9.0 g) in water (100 mls) was added to a solution of methyl 2-(2,3-dihydro-2-isopropyl-4-oxo-4H-1-benzopyran-6-yl)propionate (9.0 g) in ethanol (100 mls) and the mixture was refluxed overnight. The ethanol was removed on a 'Rotavapor' and the aqueous phase was washed with ether(2x), acidified with dilute hydrochloric acid and extracted with ether(3x). The combined ethereal extracts were washed with saturated brine solution, dried over anhydrous magnesium sulphate and evaporated to yield a red oil (6.8 g). This red oil was taken up in ether and dicyclohexylamine (4.7 g) was added. The precipitate was collected and recrystallised from ethyl acetate to yield 2-(2,3-dihydro-2-isopropyl-4-oxo-4H-1-benzopyran-6-yl)propionic acid dicyclohexamine salt as a white crystalline solid. This solid was suspended in ether and dilute hydrochloric acid was added until no more dicyclohexylamine hydrochloride was precipitated. The solid was filtered and the solvent was evaporated to yield 2-(2,3-dihydro-2-isopropyl-4-oxo-4H-1-benzopyran-6-yl)propionic acid as a red oil (2.7 g). This oil was recrystallised from ether/n-hexane (1:4) to yield 2-(2,3-dihydro-2-isopropyl-4-oxo-4H-1-benzopyran-6-yl)propionic acid as a white microcrystalline solid (0.5 g; 5%) mp. 94°–95° C.

Found: C 68.3%; H 6.8%. $C_{15}H_{15}O_4$ requires: C 68.6%; H 9.6%.

Nmr, ir and m.s. consistent with the proposed structure.

EXAMPLE 8

The following compounds were also prepared by the procedures indicated using appropriate starting materials:

(a) 2-(2,3-Dihydro-4-oxo-4H-1-benzopyran-6-yl)propionic acid mp 121°–2° C.
Prepared by the process of Example 5.
Starting material—2-(4-oxo-4H-1-benzopyran-6-yl)propan-1-ol (b) 2-[2,3-Dihydro-2-(prop-1-yl)-4-oxo-4H-1-benzopyran-6-yl] propionic acid mp 81°–3° C.
Prepared by the process of Example 5.
Starting material—2-(2-propyl-4-oxo-4H-1-benzopyran-6-yl) propan-1-ol (c) 2-(2,3-Dihydro-3-methyl-4-oxo-4H-1-benzopyran-6-yl) propionic acid mp 70°–73° C.
Prepared by the process of Example 7.
Starting material—propionyl chloride and using ethyl formate in place of ethyl isobutyrate in step (b).
Theory for $C_{12}H_{14}O_4$: C, 66.65% H, 6.0%. Found: C, 66.6% H, 6.2%.
(d) 2-(2,3-Dihydro-2-phenyl-4-oxo-4H-1-benzopyran-6-yl) propionic acid mp 168°–9° C.
Prepared by the process of Example 6.
Starting material—cinnamoyl chloride
(e) 2-(2,3-Dihydro-2-methyl-4-oxo-4H-1-benzopyran-6-yl) propionic acid mp 108°–9° C.
Prepared by the process of Example 6.
Starting material—crotonyl chloride
(f) 2-(2-Propyl-4-oxo-4H-1-benzopyran-6-yl)propan-1-ol
Prepared by the process of Example 3(e)
I.R. carbonyl absorption at 1650 cm$^{-1}$
Starting material—ethyl butyrate
(g) 2-(4-Oxo-4H-1-benzopyran-6-yl)propan-1-ol
Prepared by the process of Example 3(e)
I.R. carbonyl absorption at 1660 cm$^{-1}$
Starting material—ethyl formate.

EXAMPLE 9

2-[2-(1,1-Dimethylethyl)-4-oxo-4H-1-benzopyran-6-yl]propionic acid (a) Methyl 2-(3-acetyl-4-hydroxyphenyl)propionate Titanium tetrachloride (82.3 mls) was added dropwise to a stirred solution of methyl 2-(4-methoxyphenyl)propionate (25 g) in dry dichloromethane (250 mls), cooled in an ice/salt-bath, at a rate sufficient to maintain the temperature between −10° C. and −5° C. The mixture was stirred for 10 minutes and acetyl chloride (10 g) was added dropwise at a rate sufficient to maintain the temperature below 0° C. The solution was stirred at −5° C. for 1½ hours when boron trichloride (15 mls) was added. Stirring was continued for ½ hour at +3° C. before pouring on to crushed ice/concentrated hydrochloric acid and separating the two phases. The aqueous phase was extracted with ether (3x) and the combined organic extracts were washed with saturated sodium bicarbonate solution, saturated brine solution, and dried over anhydrous magnesium sulphate. Evaporation of the solvent yielded the crude product as a pale yellow oil. Vacuum distillation furnished a pale yellow oil bp 120°–125° C./0.15 mm (16.2 g; 59%)

The i.r. spectrum showed carbonyl bands at 1643 and 1735 cm$^{-1}$ (b) Ethyl 2-[2-(1,1-dimethylethyl)-4-oxo-4H-1-benzopyran-6-yl]propionate.

Methyl-2-(3-acetyl-4-hydroxyphenyl)propionate (2.22 g; 10 m.mole) was added, with stirring and cooling (temperature <20° C.) under dry nitrogen, to a suspension of oil free sodium hydride (0.96 g; 40 m.mole) in dry hexamethyl-phosphoric triamide (25 ml). The resulting mixture was stirred at room temperature for 1½ hours, after which time ethylpivalate (2.56 g; 3.0 ml; 20 m.mole) in dry hexamethyl-phosphoric-triamide (10 ml) was added dropwise, with stirring. The resulting mixture was stirred at room temperature for 2 hours, heated to 70° C. for 4½ hours, and set aside at room temperature overnight. The reaction mixture was poured into water (350 ml) acidified with conc. hydrochloric acid (20 ml) and extracted with ether (3×100 ml). The combined organic extracts were washed with 1N hydrochloric acid, water and brine, dried (Na$_2$SO$_4$) and concentrated in vacuo affording an oil.

The oil was taken up in ethanol (50 ml) and heated to reflux with conc. hydrochloric acid (5 ml) for 2 hours. The cooled reaction mixture was poured into water (600 ml), saturated with salt, and extracted with ether (3×100 ml). The combined ethereal extracts were washed with water and brine, dried (Na$_2$SO$_4$) and concentrated in vacuo affording the crude product, which was chromatographed on silica gel (200 g) using ether as eluant. The pure product was obtained as a brown oil (1.22 g)

nmr: 1.8–2.7 τ 3H Aromatic ABX System. 3.74 τ 1H Singlet; chromone 3-H.

(c) 2-[2-(1,1-Dimethylethyl)-4-oxo-4H-1-benzopyran-6-yl]propionic acid

Ethyl-2-[2-(1,1-dimethylethyl)-4-oxo-4H-1-benzopyran-6-yl] propionate (3.64 g) was taken up in ethanol (40 ml) and heated to reflux for 30 hours with 5% aqueous sodium bicarbonate solution (15 ml). After cooling the majority of the ethanol was removed in vacuo, the residue was dissolved in water (500 ml) and washed with ether (2×100 ml). The aqueous phase was acidified and extracted with ether (3×100 ml). The combined ethereal extracts were washed with water and brine, dried (Na$_2$SO$_4$) and concentrated in vacuo affording the crude product which was recrystallised from ethylacetate-hexane affording the title compound 1.91 g mp 147°–50° C.

Theory for: $C_{16}H_{18}O_4$ C=70.04% H=6.6%. Found: C=70.4% M=6.9%.

EXAMPLE 10

2-[2,3-Dihydro-2-(1,1-dimethylethyl)-4-oxo-4H-1-benzopyran-6-yl]propionic acid (a) Ethyl-2-[2,3-dihydro-2-(1,1-dimethylethyl)-4-oxo-4H-1-benzopyran-6-yl]propionate Ethyl-2-[2-(1,1-dimethylethyl)-4-oxo-4H-1-benzopyran-6-yl]propionate (6.61 g) was taken up in dry ethanol (150 ml) and hydrogenated at 85 p.s.i. with 5% palladium on carbon (0.2 g) and 5% palladium on barium sulphate (0.4 g) for a total of 48 hours. The catalyst was removed by filtration ('Hyflo' supercel) and the ethanol removed in vacuo affording an oil. The oil was taken up in acetone (50 ml) and treated with a slight excess of Jones reagent. The excess oxidant was destroyed with methanol and the reaction mixture was dissolved in water (200 ml) and extracted with ether. The combined ethereal extracts were washed with water, dilute aqueous sodium bicarbonate solution and water, dried (MgSO$_4$) and concentrated in vacuo to give the title compound as an oil - 6 g.

nmr: 2.3–3.3τ—3H—ABX of aromatics.~7.5τ—2-H—AB of ABX of chromanone 2-3 positions.

(b) 2-[2,3-Dihydro-2-(1,1-dimethylethyl)-4-oxo-4H-1-benzopyran-6-yl]propionic acid Ethyl-2-[2,3-dihydro-2-(1,1-dimethylethyl)-4-oxo-4H-1-benzopyran-6-yl]propionate (6 g) was dissolved in ethanol (200 ml) and heated to reflux with dilute aqueous sodium bicarbonate solution (50 ml) for eight hours. The reaction mixture was poured into water, acidified and extracted with ether. The combined ethereal extracts were washed with water and dried (MgSO₄) and concentrated in vacuo affording a mixture of the desired product and starting material which were separated by chromatography on silica gel using dichloromethane/ether mixtures as eluant. The title compound was recrystallised from petroleum ether (bp 40°-60° C.) as a white solid: 1.4 g, mp 117°-8° C.

Theory for: $C_{16}H_{20}O_4$ C=69.5 H=7.3. Found: C=69.4 H=7.4.

EXAMPLE 11

2-(2,3-Dihydro-2-ethyl-7-methoxy-4-oxo-4H-1-benzopyran-6-yl) propionic acid

(a) Ethyl 2-(2,4-dimethoxy phenyl)-2-hydroxy propionate

Dry magnesium turnings (10.02 g: 0.42 gm atom) were covered with dry ether and methyl iodide (60 g; 26.3 ml; 0.42 mole) in dry ether (30 ml) was added over a period of 3 hours with vigorous stirring under dry nitrogen. The resulting methyl magnesium iodide was added dropwise (with filtration) to a solution of ethyl-2,4-dimethoxyphenylglyoxylate (31.5 g; 0.135 mole) in dry ether (400 ml) with stirring whilst maintaining the temperature below 20° C. After the addition was completed the reaction mixture was heated to reflux for ¼ hour cooled, and poured into 0.2 N sulphuric acid (1200 ml) with vigorous stirring. The ether was separated and the aqueous phase extracted with ether (2×300 ml). The combined ethereal extracts were washed with water, an aqueous solution of potassium iodide and sodium thiosulphate, water and brine, dried (Na₂SO₄) and concentrated in vacuo to afford the title compound: 27.1 g:

$\nu_{OH}$:—3500 cm⁻¹
$\nu_{CO}$:—1730 cm⁻¹

(b) Ethyl 2-(2,4-dimethoxyphenyl)propenoate

Ethyl-2-(2,4-dimethoxyphenyl)-2-hydroxy propionate (27.0 g crude from (a) above) was dissolved in benzene (300 ml) and heated to reflux, using a Dean Stark water separator, with p-toluene sulphonic acid (0.5 g) for 6 hours. The benzene solution was washed with 5% aqueous sodium bicarbonate solution, water and brine, dried (Na₂SO₄) and concentrated in vacuo to afford the title compound 23.0 g.

NMR τ: 3.92—IH—olefinic methylene.
4.47—IH—olefinic methylene.

(c) Ethyl 2-(2,4-dimethoxyphenyl)propionate

Ethyl-2-(2,4-dimethoxyphenyl)propenoate (22.8 g— from step (b) above) was taken up in ethanol (300 ml) and hydrogenated at atmospheric pressure and room temperature with platinum oxide (0.6 g). The catalyst was removed by filtration (using 'Hyflo' supercel), the ethanol evaporated in vacuo and the residue distilled affording the title compound: 12.64 g, bp 110°-5° C./0.25 mm NMR τ: 8.65-8.8—3H—doublet J=7H$_z$.

(d) 2-(2,3-Dihydro-2-ethyl-7-methoxy-4-oxo-4H-1-benzopyran-6-yl) propionic acid Titanium tetrachloride (51 g; 31 ml; 0.27 mole) was added dropwise with stirring and cooling (−20° C.) to a solution of ethyl 2-(2,4-dimethoxyphenyl)propionate (12.6 g; 0.0532 mole) in dry dichloromethane (200 ml) and stirring continued for ½ hour. Pent-2-enoylchloride (6.5; 0055 mole) in dry dichloromethane (40 ml) was added dropwise with stirring and cooling (−20° C.), and stirring was continued for a further 1 hour at room temperature.

The reaction mixture was again cooled to −20° C. and boron trichloride (25 ml) added in one portion. The reaction mixture was allowed to warm gradually to room temperature, poured on to a a mixture of crushed ice (1 ltr) and concentrated hydrochloric acid (50 ml) and stirred vigorously to decompose the organometallic complexes. The dichloromethane was separated and the aqueous phase extracted with dichloromethane (2×300 ml). The combined organic extracts were washed with water, 5% aqueous sodium bicarbonate solution, and water, dried (Na₂SO₄) and concentrated in vacuo affording crude ethyl 2-[4-hydroxy-3-(pent-2-en-1-oyl) phenyl]propionate (15.74 g) as an oil.

The oil (6.6 g) was taken up in ethanol (100 ml) and stirred at room temperature for 5 hours with 10% aqueous sodium hydroxide solution (20 ml). The reaction mixture was poured into water (600 ml) and extracted with ether (which was discarded). The aqueous phase was acidified with hydrochloric acid and extracted with ether (3×100 ml). The combined ethereal extracts were washed with water and brine, dried (Na₂SO₄) and concentrated in vacuo affording the crude product: 5.13 g.

Trituration of the crude product with ether-petroleum ether (bp 40°-60° C.) afforded a grey-brown solid which upon trituration with a small volume of ether afforded a reasonably pure product: 2.17 g. Recrystallisation of this product from propan-2-ol: petroleum ether (bp 40°-60° C.) afforded the title compound:

1.55 g mp 158°-60° C.

Theory for: $C_{15}H_{18}O_5$ C=64.7 H=6.5. Found: C=64.4 C=6.6.

EXAMPLE 12

2-(2,3-Dihydro-2-ethyl-4-oxo-4H-1-benzopyran-6-yl)propionamide

To a stirred solution of 2-(2,3-dihydro-2-ethyl-4-oxo-4H-1-benzopyran-6-yl)propionic acid (10.0 g; 0.04 mol) in dry tetrahydrofuran (100 ml) at −20° C. was added triethylamine (4.05 g; 0.04 mol) followed by ethyl chloroformate (6.0 g; 0.056 mol). After 10 minutes the mixture was saturated with gaseous ammonia. It was then acidified with dilute hydrochloric acid, the organic solvent was removed in vacuo and the product was extracted with chloroform (4×80 ml). The combined extracts were washed with water (2×100 ml), brine (200 ml), and dried over MgSO₄. Evaporation of the solvent and recrystallisation of the residue from ethyl acetate gave the title compound (wt=5.1 g). m.p. 148°-150° C.

Found: C, 67.7% H, 7.1%; N, 5.8%. $C_{14}H_{17}NO_3$ requires: C, 68.0%; H, 6.9%; N, 5.7%.

EXAMPLE 13

(a) 2-[2-(2-Methylpropyl)-4-oxo-4H-1-benzopyran-6-yl]propionic acid m.p. 108°-109°

Prepared by the process of Example 9, using ethyl isovalerate in place of ethyl pivalate in step (b).

(b) 2-(2-Isopropyl-4-oxo-4H-1-benzopyran-6-yl)propionic acid m.p. 127°-128°

Prepared by the process of Example 9, using ethyl isobutyrate in place of ethyl pivalate in (b).

Found: C, 69.0%; H, 6.1%. C$_{15}$H$_{16}$O$_4$ requires: C, 69.2% H, 6.2%.

(c) 2-(4-Oxo-2-phenyl-4H-1-benzopyran-6-yl)propionic acid m.p. 220°–221°

Prepared by the process of Example 9, using methyl benzoate in place of ethyl pivalate in step (b).

Found: C, 73.2%; H, 5.0%. C$_{18}$H$_{14}$O$_4$ requires: C, 73.5% H, 4.8%.

(d) 2-(3-Methyl-4-oxo-4H-1-benzopyran-6-yl)propionic acid m.p. 188°–189°

Prepared by the process of Example 9, using propionyl chloride in place of acetyl chloride in step (a), and using ethyl formate in place of ethyl pivalate in step (b).

Found: C, 67.0%; H, 5.3%. C$_{13}$H$_{12}$O$_4$ requires: C, 67.3%; H, 5.2%.

(e) 2-(4-Oxo-3-phenyl-4H-1-benzopyran-6-yl)propionic acid m.p. 169°–170°

Prepared by the process of Example 9, using phenylacetyl chloride in place of acetyl chloride in step (a), and using ethyl formate in place of ethyl pivalate in step (b).

Found: C, 73.2%; H, 4.8%. C$_{18}$H$_{14}$O$_4$ requires: C, 73.5%; H, 4.8%.

EXAMPLE 14

(a) 2-(8-Chloro-2,3-dihydro-2-ethyl-4-oxo-4H-1-benzopyran-6-yl) propionic acid m.p. 92° C.

Prepared by the process of Example 10(a). Starting material—ethyl 2-(8-Chloro-2-ethyl-4-oxo-4H-1-benzopyran-6-yl)propionate.

Found: C, 59.6% H, 5.5% Cl 12.35%. C$_{14}$H$_{15}$ClO$_4$ requires: C, 59.5% H, 5.3% Cl 12.6%.

(b) 2-[2,3-Dihydro-2-(2-methylpropyl)-4-oxo-4H-1-benzopyran-6-yl]propionic acid m.p. 115°–117°

Prepared by the process of Example 10, using Raney Nickel at 45 p.s.i. in place of Pd-C/Pd-BaSO$_4$ catalyst in step (a).

Starting material—ethyl 2-[2-(2-methylpropyl)-4-oxo-4H-1-benzopyran-6-yl]propionate.

Found: C, 69.6%; H, 7.6%. C$_{16}$H$_{20}$O$_4$ requires: C, 69.5%; H, 7.3%.

(c) 2-(2,3-Dihydro-4-oxo-3-phenyl-4H-1-benzopyran-6-yl) propionic acid

Prepared by the process of Example 10, using Raney Nickel at 45 p.s.i. in place of Pd-C/Pd-BaSO$_4$ catalyst in step (a).

Starting material—methyl 2-(4-oxo-3-phenyl-4H-1-benzopyran-6-yl)propionate.

Found: C, 73.0%; H, 5.8%. C$_{18}$H$_{16}$O$_4$ require: C, 72.9%; H, 5.4%.

EXAMPLE 15

2-(2-Ethyl-3-methyl-4-oxo-4H-1-benzopyran-6-yl)propionic acid (a) Methyl 2-(2-ethyl-3-methyl-4-oxo-4H-1-benzopyran-6-yl) propionate A mixture of methyl 2-(4-hydroxy-3-propionylphenyl) propionate (10 g) and fused sodium propionate (5 g) was refluxed in propionic anhydride (22 mls) for 3 hours. After cooling, water (150 mls) was added and the mixture was extracted with ether (3×100 mls). The combined etheral solutions were washed with water (3×50 mls), dried with anhydrous magnesium sulphate and evaporated to yield the crude methyl 2-(2-ethyl-3-methyl-4-oxo-4H-1-benzopyran-6-yl) propionate as a red oil. Vacuum distillation furnished a pale green oil bp 180°–185° C./0.1 mm (9.5 g; 82%).

The i.r. spectrum showed carbonyl bands at 1640 cm$^{-1}$ and 1735 cm$^{-1}$.

(b) 2-(2-Ethyl-3-methyl-4-oxo-4H-1-benzopyran-6-yl)propionic acid

A solution of methyl 2-(2-ethyl-3-methyl-4-oxo-4H-1-benzopyran-6-yl)propionate (1 g) in ethanol (120 mls), and sodium bicarbonate (1 g) in water (30 mls) was refluxed for 20 hours. The ethanol was removed on a 'Rotavapor' and the residue was washed with ether (3×50 mls). After acidification with dilute hydrochloric acid, the aqueous phase was extracted with ethyl acetate (3×50 mls), which was washed with brine solution (3×30 mls), dried over anhydrous magnesium sulphate and evaporated to yield an off-white solid. This was recrystallised from ethyl acetate to yield the product as a pale yellow solid (0.4 g; 42%), mp 196°–198° C.

The i.r. spectrum showed carbonyl bands at 1638 cm$^{-1}$ and 1700 cm$^{-1}$

Calculated C 69.2% H 6.2% for C$_{15}$H$_{16}$O$_4$. Found C 68.9% H 6.5%.

EXAMPLE 16

2-[2,3-Dihydro-2-ethyl-3-methyl-4-oxo-4H-1-benzopyran-6-yl]propionic acid (a) Methyl 2-[2,3-dihydro-2-ethyl-3-methyl-4-oxo-4H-1-benzopyran-6-yl]propionate Methyl 2-[2-ethyl-3-methyl-4-oxo-4H-1-benzopyran-6-yl]propionate (6.61 g) was taken up in dry ethanol (150 ml) and hydrogenated at 85 p.s.i. with 5% palladium on carbon (0.2 g) and 5% palladium on barium sulphate (0.49) for a total of 48 hours. The catalyst was removed by filtration ('Hyflo' supercel) and the ethanol removed in vacuo affording an oil. The oil was taken up in acetone (50 ml) and treated with a slight excess of Jones reagent. The excess oxidant was destroyed with methanol and the reaction mixture was dissolved in water (200 ml) and extracted with ether. The combined ethereal extracts were washed with water, dilute aqueous sodium bicarbonate solution and water, dried (MgSO$_4$) and concentrated in vacuo to give the title compound as an oil—6 g.

(b) 2-[2,3-Dihydro-2-ethyl-3-methyl)-4-oxo-4H-1-benzopyran-6-yl]propionic acid

Methyl 2-[2,3-dihydro-2-ethyl-3-methyl-4-oxo-4H-1-benzopyran-6-yl]propionate (6 g) was dissolved in ethanol (200 ml) and heated to reflux with dilute aqueous sodium bicarbonate solution (50 ml) for eight hours. The reaction mixture was poured into water, acidified and extracted with ether. The combined etheral extracts were washed with water and dried (MgSO$_4$) and concentrated in vacuo affording a mixture of the desired product and starting material which were separated by chromatography on silica gel using dichloromethane/ether mixtures as eluant. The title compound was recrystallised from petroleum ether (bp 40°–60° C.) as a white solid: 1.4 g, mp 114°–115° C.

Theory for: C$_{15}$H$_{18}$O$_4$ C=68.7 H=6.9%. Found: C=68.9 H=7.1%.

We claim:

1. A compound of the formula

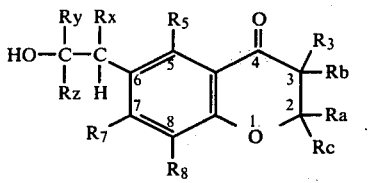

in which Ra is hydrogen, alkyl, alkenyl or phenyl,
R$_3$, R$_5$, R$_7$ and R$_8$, which may be the same or different, are each hydrogen, alkyl, alkoxy, halogen, hydroxy, alkenyl or phenyl,
Rx is alkyl,
Ry and Rz are both hydrogen, or together represent a carbonyl oxygen atom,
Rb and Rc are both hydrogen, or together represent a carbon-carbon bond,
Ra, Rx, R$_3$, R$_5$, R$_7$ and R$_8$ each containing up to 10 carbon atoms,
and, where Ry and Rz form carbonyl, pharmaceutically acceptable salts, esters having alcoholic residues containing up to 10 carbon atoms, and unsubstituted or mono- or di-alkyl C 1 to 6 amides thereof.

2. A compound according to claim 1, wherein Rb and Rc both represent hydrogen.

3. A compound of the formula

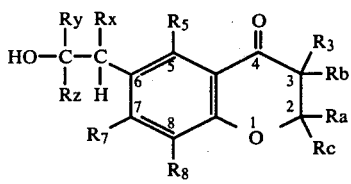

in which Ra is hydrogen, alkyl, or alkenyl,
R$_3$, R$_5$, R$_7$ and R$_8$, which may be the same or different, are each hydrogen, alkyl, alkoxy, halogen, hydroxy, alkenyl or phenyl,
Rx is alkyl,
Ry and Rz are both hydrogen, or together represent a carbonyl oxygen atom,
Rb and Rc are both hydrogen,
Ra, Rx, R$_3$, R$_5$, R$_7$ and R$_8$ each containing up to 10 carbon atoms,
and, where Ry and Rz form carbonyl, pharmaceutically acceptable salts, esters having alcoholic residues containing up to 10 carbon atoms, and unsubstituted or mono- or dialkyl C 1 to 6 amides thereof.

4. A compound according to claim 3, wherein Ra, Rx, R$_3$, R$_5$, R$_7$ and R$_8$ each contain up to 6 carbon atoms.

5. A compound according to claim 3, wherein Ra contains 2 to 6 carbon atoms.

6. A compound according to claim 3, wherein Ra is straight or branched alkyl C 2 to 4.

7. A compound according to claim 3, wherein Ra is ethyl, isopropyl, n-propyl, or hydrogen.

8. A compound according to claim 3, wherein R$_3$ is hydrogen.

9. A compound according to claim 3, wherein R$_5$, R$_7$ and R$_8$ are hydrogen, hydroxy, alkoxy, alkyl or halogen.

10. A compound according to claim 3, wherein each of R$_5$, R$_7$ and R$_8$ are hydrogen.

11. A compound according to claim 3, wherein Rx contains 1 or 2 carbon atoms.

12. A compound according to claim 3, wherein Rx is methyl.

13. A compound according to claim 3, wherein Ry and Rz together form a carbonyl oxygen atom.

14. A compound according to claim 3, which is
2-(2-Ethyl-4-oxo-4H-1-benzopyran-6-yl)propan-1-ol,
2-(2-Ethyl-4-oxo-4H-1-benzopyran-6-yl)propionic acid,
2-(2,3-Dihydro-2-ethyl-4-oxo-4H-1-benzopyran-6-yl)propanol,
2-(2,3-Dihydro-2-ethyl-4-oxo-4H-1-benzopyran-6-yl)propionic acid,
2-(2,3-Dihydro-4-oxo-4H-1-benzopyran-6-yl)propionic acid,
2-[2,3-Dihydro-2-(prop-1-yl)-4-oxo-4H-1-benzopyran-6-yl]propionic acid,
2-(2,3-Dihydro-3-methyl-4-oxo-4H-1-benzopyran-6-yl)propionic acid,
2-(2,3-Dihydro-2-methyl-4-oxo-4H-1-benzopyran-6-yl)propionic acid,
2-(2-Propyl-4-oxo-4H-1-benzopyran-6-yl)propan-1-ol,
2-(4-Oxo-4H-1-benzopyran-6-yl)propan-1-ol,
2-[2-(1,1-Dimethylethyl)-4-oxo-4H-1-benzopyran-6-yl]propionic acid,
2-[2,3-Dihydro-2-(1,1-dimethylethyl)-4-oxo-4H-1-benzopyran-6-yl]propionic acid,
2-(2,3-Dihydro-2-ethyl-7-methoxy-4-oxo-4H-1-benzopyran-6-yl)propionic acid,
2-(2,3-Dihydro-2-ethyl-4-oxo-4H-1-benzopyran-6-yl)propionamide,
2-[2-(2-Methylpropyl)-4-oxo-4H-1-benzopyran-6-yl]propionic acid,
2-(2-Isopropyl-4-oxo-4H-1-benzopyran-6-yl)propionic acid,
2-(3-Methyl-4-oxo-4H-1-benzopyran-6-yl)propionic acid,
2-(8-Chloro-2,3-dihydro-2-ethyl-4-oxo-4H-1-benzopyran-6-yl)propionic acid,
2-[2,3-Dihydro-2-(2-methylpropyl)-4-oxo-4H-1-benzopyran-6-yl]propionic acid,
2-(2-Ethyl-3-methyl-4-oxo-4H-1-benzopyran-6-yl)propionic acid, or
2-[2,3-Dihydro-2-ethyl-3-methyl-4-oxo-4H-1-benzopyran-6-yl]propionic acid.

15. A compound according to claim 3, which is 2-(2,3-dihydro-2-isopropyl-4-oxo-4H-1-benzopyran-6-yl)propionic acid.

* * * * *